US00PP18341P3

(12) United States Plant Patent
Dirr

(10) Patent No.: US PP18,341 P3
(45) Date of Patent: Dec. 25, 2007

(54) ***HYDRANGEA MACROPHYLLA* PLANT NAMED 'HYMMAD III'**

(50) Latin Name: *Hydrangea macrophylla*
Varietal Denomination: HYMMAD III

(75) Inventor: Michael A. Dirr, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 98 days.

(21) Appl. No.: 11/348,284

(22) Filed: Feb. 6, 2006

(65) Prior Publication Data

US 2007/0186316 P1 Aug. 9, 2007

(51) Int. Cl.
*A01H 5/00* (2006.01)

(52) U.S. Cl. ..... Plt./250

(58) Field of Classification Search ..... Plt./250
See application file for complete search history.

(56) References Cited

U.S. PATENT DOCUMENTS

PP15,298 P3 * 11/2004 Black ..... Plt./250

* cited by examiner

*Primary Examiner*—Wendy C. Haas
(74) *Attorney, Agent, or Firm*—Greenlee Winner and Sullivan, PC

(57) ABSTRACT

*Hydrangea macrophylla,* 'HYMMAD III' has large, pure white lacecap inflorescences that respond slightly with maturation to the absence and presence of aluminum becoming pink or blue, respectively. The habit is upright and strong stems that hold the inflorescences erect. The large, lustrous, dark green leaves are highly mildew and Cercospora resistant, as well as frost resistant.

2 Drawing Sheets

Botanical classification: *Hydrangea macrophylla.*
Varietal denomination: 'HYMMAD III'.

BACKGROUND OF THE INVENTION

The present invention relates to a new and distinct cultivar of *Hydrangea macrophylla,* a member of the Hydrangeaceae family, hereinafter referred to as 'HYMMAD III'. This cultivar is grown primarily as an ornamental for landscape use and for use as a potted plant, fresh cut and dried flowers. The cultivar originated from open-pollination of *Hydrangea macrophylla* 'Veitchii' (non-patented), the pollen donor being unknown. It was selected at the University of Georgia, Athens, Ga. in 2001, from the progeny seedlings of this open pollination by continued evaluation for white lacecap flowers that mature to light pink or blue in the absence or presence of aluminum (Al), respectively, increased resistance to mildew, and improved habit, leaf, and stem characteristics.

'HYMMAD III' is distinguished from its female parent 'Veitchii' by its pure white, larger lacecap inflorescence that turns light pink or blue in the absence or presence, respectively, of Al. The sepals always open white and latently respond to Al. 'HYMMAD III' has lustrous dark green leaves, up to 26 cm long, much larger than 'Veitchii' (16 cm). 'HYMMAD III', like 'Veitchii', is highly mildew and Cercospora resistant, but it grows faster, has stronger stems, and larger, showier inflorescences. The flattened lacecap inflorescence averages 12 to 15 cm in diameter, about 25% larger than those of 'Veitchii'.

'HYMMAD III' is distinguished from lacecaps such as 'White Wave' (unpatented) and 'Lanarth White' (unpatented) by its larger inflorescence, its larger and darker green leaves and its high resistance to mildew.

SUMMARY OF THE INVENTION

The following traits have been observed and represent the characteristics of the new Cultivar. In combination these characteristics distinguish 'HYMMAD III' from all other varieties in commerce known to the inventor:

1) Pure white flowers (sepals) that are slightly affected by the absence or presence of Al, turning pink or light blue, respectively, unlike 'Veitchii' which never develops the blue coloration.
2) Large, up to 15 cm lacecap inflorescences with 2.5 cm diameter sepalous ray florets and mauve to purple fertile flowers in the center.
3) Upright habit with strong stems that hold the inflorescences erect.
4) Lustrous, dark green leaves.
5) Mildew and Cercospora resistant foliage similar to its parent, 'Veitchii'. 'HYMMAD III' is essentially immune to mildew and Cercospora leaf diseases.
6) Superior vigor and disease resistance allow commercial production of an 11 liter container plant in a single growing season.
7) Foliage is more frost resistant than standard cultivars like 'Nikko Blue' (non-patented), 'Bailmer' (PP 15,298) and 'Lilacina' (non-patented). 'HYMMAD III' tolerated 26° F. in November in Athens, Ga.

'HYMMAD III' has been asexually propagated in Athens, Ga. since 2001. The characteristics of the cultivar have been stable and reproduced true-to-type in successive vegetative generations.

BRIEF DESCRIPTION OF THE PHOTOGRAPHS

BOTANICAL DESCRIPTION OF THE PLANT

Figure 1:
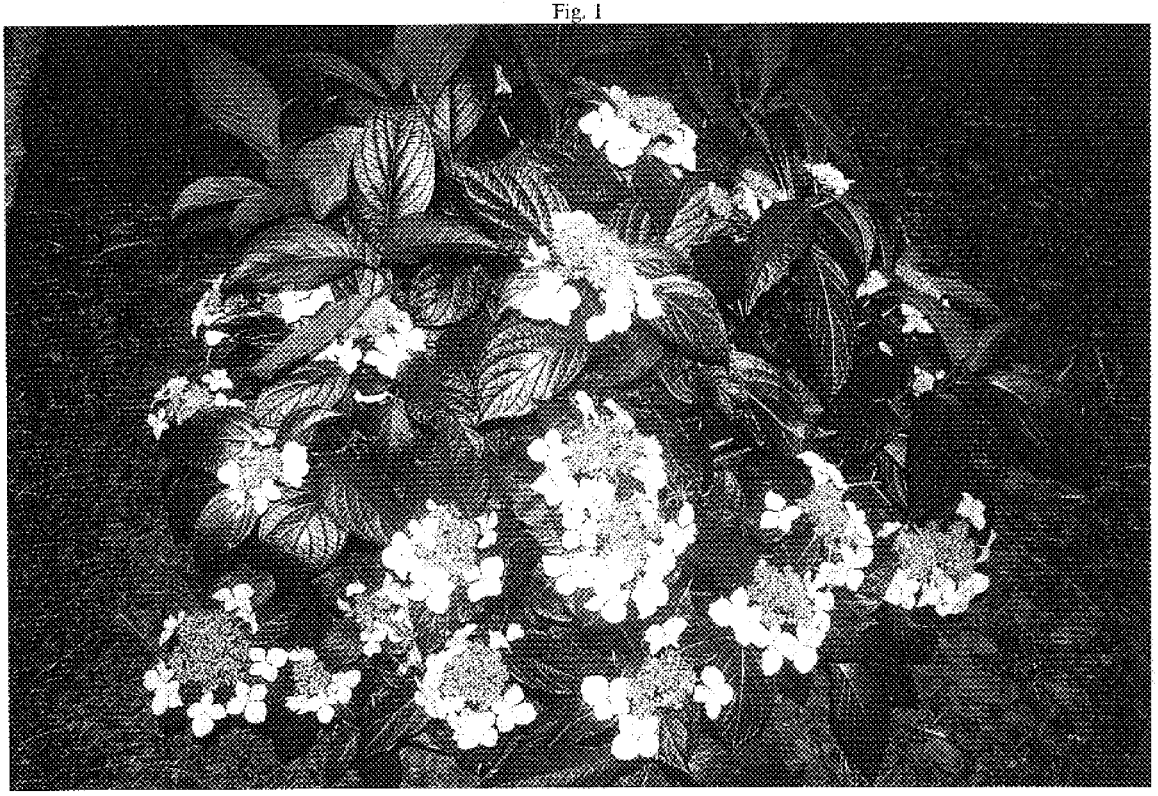
FIG. 1 shows a 3 year-old plant growing in the ground in Dearing, Ga., taken on May 27, 2004 showing the habit with lace cap inflorescence with white sepals and purple fertile flowers and lustrous, dark green leaves.
Figure 2:
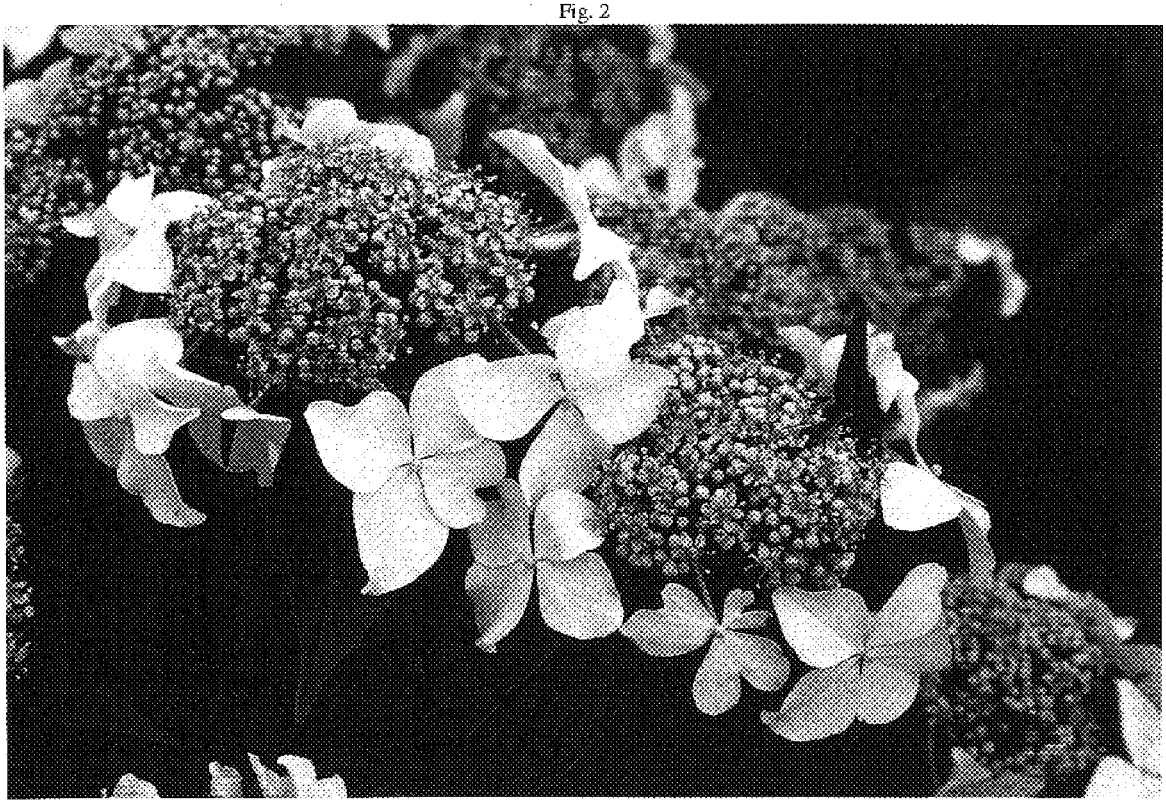
FIG. 2 shows an inflorescence aging to pink on plant grown in the absence of Al.

A detailed description of *Hydrangea macrophylla* 'HYMMAD III' follows. Colors are based on The Royal Horticultural Colour Chart (1995). All measurements/characteristics were taken from 2 year-old plants growing in 11.8 liter containers under 50% shade at Athens, Ga., USDA Zone 7. Measurements of leaf/stems and floral characteristics are based on 10 to 20 samples. The presence of Al means that the plant was treated with aluminum sulphate (42 g per 3.8 liter of water) applied as a soil drench when flower buds were visible.

Plant:

The plant has an upright growth habit, with many upright branches from the base, attaining a size of 80 cm high by 100 cm wide after 2 years.

Stems:

Current year stems are round, averaging 5.3 mm in diameter, with no pubescence and smooth. They are Greyed-Orange 164A in color. The average internode length is 8.3 cm. Two year-old stems average 9 mm in diameter, with no pubescence but flaky texture. They are Greyed-Brown 199D/Greyed-Brown N199D in color with Brown 200A flakes.

Vegetative buds:

The conical, lateral vegetative buds are in an opposite arrangement, 2 per node at a 45° angle to the stem. They are 7 mm by 3 mm, and have 2 scales which are Greyed-Yellow 161A to Greyed-Orange 165B in color.

Flower buds:

The flower buds are round in shape with no pubescence, 3 mm by 3 mm by 3 mm and are Purple 77D with Violet-Blue 96A along suture lines in the absence of Al, and Blue 101C in the presence of Al. They develop in the early summer.

Leaf:

The leaves, in opposite arrangement, are ovate in shape with acute base and acuminate apex, and serrate margin. The mature leaf averages 12.8 cm long by 6.8 cm wide, very thick and leathery and very waxy. The surfaces have no pubescence. The color of the emerging leaf is Yellow-Green 144A, shiny, to Green 141B, shiny, on the upper surface, and Yellow-Green 146C to Yellow-Green 144A, shiny on the lower surface, maturing to Green 139A on the upper surface and Green 137B on the lower.

The venation is pinnate, with Green 143C veins.

The petioles average 2 cm long and 3 mm in diameter, are grooved above and rounded below, and are Yellow-Green 144A in color.

Inflorescence:

The bloom period is from mid May to the end of June in Athens, Ga.

The lacecap inflorescence, containing an average of 423 fertile flowers, averages 14 cm in diameter and 6 cm in depth.

There are an average 8 inflorescences per plant, one per terminal branch.

Sterile florets:

There is an average of 10 florets per inflorescence, each with 4 sepals. The sepals are ovoid in shape with rounded apex and acute base and entire margin with occasional undulation. The texture is smooth with no pubescence. They are 25.0 mm long by 20.0 mm wide. At peak of bloom the upper surface is White N155B with touches of Purple 75C in the absence of Al, and Blue-Green 111D in the presence of Al. The lower surface is White N155B in the absence of Al, and White N155A/Blue-Green 111D in the presence of Al.

The peduncle is 5 to 10 mm long, and Greyed-Red 182D in the absence of Al, and Violet-Blue 97A in the presence of Al.

Fertile flowers:

There are 5 petals per flower. The petals are ovate in shape, with acute apex, truncate base and an entire margin. They are 3 mm in length by 2 mm wide, with a smooth texture and no pubescence. The color of the upper surface is Violet 84B with Violet-Blue 90D at the base and Violet-Blue 91A at the tip in the absence of Al, and Blue 101C with Blue 100A along the margins and at the base in the presence of Al. The lower surface is Purple 76A in the absence of Al, and Blue 101C in the presence of Al.

The pedicel is 4 mm long, finely pubescence, and Violet 85A in the absence of Al, and Violet-Blue 98C in the presence of Al.

There are 6 stamens per flower. The anther is 1 mm long by 1 mm wide and Violet-Blue 93C in the absence of Al, and Blue 102B in the presence of Al.

The filament is 2.5 mm long by 0.3 mm wide and Violet-Blue 93B in the absence of Al, and Blue 99C in the presence of Al.

The superior pistil is 3 mm long by 1 mm wide with no pubescence.

There are 3 stigmas per pistil, with no pubescence, colored Violet N87A in the absence of Al, and Violet-Blue 98A in the presence of Al.

The style in tubular in shape, 1 mm long with no pubescence and Violet 84B in the absence of Al, and Violet-Blue 97B in the presence of Al.

Fruit:

The fruit is a capsule, ovoid in shape, 4 mm long by 3 mm wide, and Green 143C in color.

Seed:

The seeds are 0.5 mm long by 0.25 mm wide and Greyed-Orange 164C in color.

I claim:

1. A new and distinct variety of *Hydrangea macrophylla* plant substantially as herein described and illustrated.

* * * * *